(12) United States Patent
Tien (10) Patent No.: US 12,220,594 B2
(45) Date of Patent: Feb. 11, 2025

(54) SYSTEM AND METHOD FOR TREATING CANCER

(71) Applicant: Robert Der-Yang Tien, Taipei (TW)

(72) Inventor: Robert Der-Yang Tien, Taipei (TW)

(*) Notice: Subject to any disclaimer, the term of this patent is extended or adjusted under 35 U.S.C. 154(b) by 1190 days.

(21) Appl. No.: 16/159,666

(22) Filed: Oct. 14, 2018

(65) Prior Publication Data

US 2019/0117991 A1  Apr. 25, 2019

Related U.S. Application Data (60) Provisional application No. 62/574,349, filed on Oct. 19, 2017.

(51) Int. Cl.
| | | |
|---|---|---|
| A61N 1/40 | (2006.01) | |
| A61B 18/04 | (2006.01) | |
| A61F 7/12 | (2006.01) | |

(52) U.S. Cl.
CPC ............ *A61N 1/403* (2013.01); *A61B 18/04* (2013.01); *A61B 2018/044* (2013.01); *A61B 2018/046* (2013.01); *A61F 7/12* (2013.01); *A61F 7/123* (2013.01)

(58) Field of Classification Search
CPC ............ A61N 1/403; A61F 2007/0054; A61F 2007/0091; A61F 2007/0092; A61F 7/12; A61F 7/123; A61F 2007/126; A61B 2018/00011; A61B 2018/00023; A61B 18/04; A61B 2018/044; A61B 2018/046; A61B 2018/144; A61B 2018/1472
See application file for complete search history.

(56) References Cited

U.S. PATENT DOCUMENTS

| | | | | |
|---|---|---|---|---|
| 5,003,991 A | * | 4/1991 | Takayama | A61N 1/36185 607/116 |
| 5,151,100 A | * | 9/1992 | Abele | A61B 18/08 607/113 |
| 6,076,012 A | * | 6/2000 | Swanson | A61N 1/06 606/41 |
| 6,589,238 B2 | * | 7/2003 | Edwards | A61B 18/1492 606/41 |
| 2005/0171527 A1 | * | 8/2005 | Bhola | A61B 18/1492 606/41 |
| 2007/0043350 A1 | * | 2/2007 | Soltesz | A61N 7/022 606/41 |
| 2009/0125014 A1 | * | 5/2009 | Bouthillier | A61B 18/04 606/41 |

(Continued)

*Primary Examiner* — Linda C Dvorak
*Assistant Examiner* — Bradford C. Blaise
(74) *Attorney, Agent, or Firm* — Birch, Stewart, Kolasch & Birch, LLP (57) ABSTRACT

Provided is a system, which includes: a radio frequency (RF) generator including an RF power, an RF signal generator configured to be initiated by the RF power and generates an RF signal; a heating apparatus including a first pouch having a first inlet tube, a second pouch having a second inlet tube connected to the first pouch, a first RF electrode in the first pouch and a second RF electrode in the second pouch, wherein the first RF electrode and the second RF electrode are configured to receive the RF signal; and a liquid reservoir operatively connected to the first inlet tube of the first pouch. Also provided is a method for treating a cancer in a subject in need thereof by using the system.

17 Claims, 5 Drawing Sheets

(56) References Cited

U.S. PATENT DOCUMENTS

| | | | |
|---|---|---|---|
| 2014/0005660 A1* | 1/2014 | Edwards | A61M 16/0438 606/41 |
| 2014/0371736 A1* | 12/2014 | Levin | A61B 18/082 606/28 |
| 2018/0110563 A1* | 4/2018 | Rohl | A61B 18/1445 |
| 2018/0296264 A1* | 10/2018 | Desimone | A61B 1/00151 |

* cited by examiner

SYSTEM AND METHOD FOR TREATING CANCER

CROSS-REFERENCE TO RELATED APPLICATION

Benefit is claimed to U.S. Provisional Patent Application No. 62/574,349, filed Oct. 19, 2017; the contents of which are incorporated by reference herein in their entirety.

BACKGROUND

1. Technical Field

The present disclosure relates to a system for treatment and a method for using the same, and more particularly relates to a system and a method for treating a cancer within a subject in need thereof.

2. Description of Associated Art

According to the American Cancer Society, 7.6 million people died from cancer in 2007. This disease affects people of all ages, and treatment options currently include surgery, radiation therapy, immunotherapy, cryotherapy, laser therapy, and chemotherapy. Surgery, alone or in conjunction with other treatments, is used in more than 90% of cases.

Surgery can involve partial or complete removal of an organ and/or the area affected by a cancerous tumor. However, in some cases, the tumor is inaccessible or has so completely invaded an area that surgery is not viable. In addition, accompanying therapies, such as radiation or chemotherapy, can cause serious or life-threatening side effects or affect other healthy tissue. Also, the treatments the patient can receive are limited.

Hyperthermia, which is also called thermal therapy or thermotherapy, is a type of cancer treatment in which body tissue is exposed to high temperatures up to 113° F. or 45° C. Researchers had shown that high temperatures can damage and kill cancer cells, usually with minimal injury to normal tissues (1). By killing cancer cells and damaging proteins and structures within cells, hyperthermia may shrink tumors (2).

Hyperthermia is almost always used with other forms of cancer therapy, such as radiation therapy and chemotherapy (1, 3). Hyperthermia may make some cancer cells more sensitive to radiation or harm other cancer cells that radiation cannot damage. Hyperthermia can also enhance the effects of certain anticancer drugs.

Numerous clinical trials have studied hyperthermia in combination with radiation therapy and/or chemotherapy. These studies have focused on the treatment of many types of cancer, including sarcoma, melanoma, and cancers of the head and neck, brain, lung, esophagus, breast, rectum, liver, appendix, cervix, and peritoneal lining (mesothelioma) (1, 3-7). Many of these studies, but not all, have shown a significant reduction in tumor size when hyperthermia is combined with other treatments (1, 3, 6, 7). However, not all of these studies have shown increased survival in patients receiving the combined treatments (3, 5, 7).

Hyperthermia is under study in clinical trials. However, now it is not widely available. The most common hyperthermia apparatuses often comprise two flat electrodes, and patient's body region is positioned between the two flat electrodes and is irradiated by radio frequency waves. The different conductivity of healthy and unhealthy tissue produces different energy absorptions. The healthy tissue can simply discharge the energy applied.

Based on the prior art, the wave frequencies have to penetrate through the patient's body per se. As such, the heating area would be imprecise, and the heating temperature could not be properly controlled. The known apparatuses and methods cannot focus and direct the energy to heat a specific spot, for example an area of the lesion.

There is therefore an ongoing need for a new, potent and therapeutically useful apparatus and method that are useful for treating tumors or malignant cells.

SUMMARY

In an aspect of the present application, a system for treating a mass within a subject in need thereof is provided. The system comprises: a radio frequency (RF) generator, a heating apparatus, and a liquid reservoir. The RF generator comprises an RF power, and an RF signal generator. The RF signal generator is configured to be initiated by the RF power and generate an RF signal. The heating apparatus comprises a first pouch having a first inlet tube, a second pouch having a second inlet tube connecting to the first pouch, a first RF electrode in the first pouch and a second RF electrode in the second pouch, wherein the first and the second RF electrodes are configured to receive the RF signal. The liquid reservoir is operatively connected to the first inlet tube of the first pouch and is configured to supply liquid to fill the first pouch and the second pouch.

In one embodiment of the present disclosure, the first and the second RF electrodes are connected with the RF signal generator via a wire. In another embodiment, the first and the second RF electrodes are wire-like electrodes.

In one embodiment of the present disclosure, the RF generator generates a wave with a frequency between the first RF electrode and the second RF electrode. The frequency of the wave is in a range of 0.1 MHz to 100 MHz between the first and the second RF electrodes. In another embodiment of the present disclosure, the RF generator generates a wave with a frequency in a range of 10 MHz to 100 MHz.

In one embodiment of the present disclosure, the liquid reservoir comprises a weight sensor which is configured to monitor a volume of the liquid. In some embodiments of the present disclosure, the liquid is an aqueous solution. Preferably, the aqueous solution is a physiologically acceptable buffer solution, or a salt thereof, or saline.

In one embodiment of the present disclosure, the system further comprises a temperature controller configured to control temperature of the liquid. The temperature controller comprises a temperature monitor to monitor the temperature of the liquid, and a heat exchanger to control the temperature of the liquid. In some embodiments of the present disclosure, the temperature of the liquid is controlled at 25° C.

In one embodiment of the present disclosure, the system further comprises a first pump and a second pump. The first pump is configured to draw the liquid out from the liquid reservoir into the temperature controller, and the second pump is configured to draw out the liquid in the first pouch and the second pouch, and back into the liquid reservoir.

In another aspect of the present application, a method for treating a cancer in a subject in need thereof is provided. The method comprises: providing the system of the present disclosure; positioning the first pouch into a first hollow capsule of the subject; positioning a second pouch into a second hollow capsule of the subject; filling the first pouch and the second pouch with the liquid; initiating the RF signal generator to generate an RF signal, wherein the first RF electrode and the second RF electrode receive the RF signal; and forming a wave to heat a mass of the subject within a hot zone between the first hollow capsule and the second hollow capsule to a desired temperature or temperature range.

In one embodiment of the present disclosure, the method for treating a cancer in a subject in need thereof comprises: providing the system of the present disclosure; positioning the first pouch into a first space within the subject; positioning a second pouch into a second space within the subject; filling the first pouch and the second pouch with the liquid; initiating the RF signal generator to generate an RF signal, wherein the first RF electrode and the second RF electrode receive the RF signal; and forming a wave to heat a mass of the subject within a hot zone between the first space and the second space.

In other embodiments of the present disclosure, the spaces where the pouches of the system of the present disclosure position into can be any part of interest of the body, such as a cavity formed between the tissues or organs of the subject, or lumen inside the body of the subject, or outside the body of the subject.

In one embodiment of the present disclosure, the mass to be heated in the subject is located between the first hollow capsule and the second hollow capsule, or between the first space and the second space where the pouches of the system of the present disclosure are positioned into. The mass of the subject is heated up to a range of at least 38° C. In another embodiment of the present disclosure, the mass of the subject is heated up to no more than 45° C. In yet another embodiment of the present disclosure, the mass of the subject is heated to a range of temperatures between 38° C. and 45° C., such as between 40° C. and 41° C. Preferably, the mass of the subject is heated up to about 42° C. In one embodiment of the present disclosure, the mass is tumor and/or malignant cells, and the cancer is pancreatic cancer, lung cancer or prostate cancer. In another embodiment of the present disclosure, if the cancer is pancreatic cancer, then the first hollow capsule is stomach of the subject and the second hollow capsule is duodenum of the subject.

BRIEF DESCRIPTION OF THE DRAWINGS

The present disclosure can be more fully understood by reading the following detailed description of the embodiments, with reference made to the accompanying drawings, wherein.

DETAILED DESCRIPTION OF THE EMBODIMENTS

The following specific examples are used to exemplify the present disclosure. A person of ordinary skill in the art can conceive the other advantages and effects of the present disclosure, based on the specification of the present disclosure. The present disclosure can also be implemented or applied as described in different specific examples. It is possible to modify and/or alter the above examples for carrying out this disclosure without contravening its spirit and scope, for different aspects and applications.

It should be noted that the structures, proportions, sizes and the like shown in the attached drawings are to be considered only in conjunction with the contents of this specification to facilitate understanding and reading for those skilled in the art, and are not intended to limit the scope of the present disclosure. Thus, they do not hold any real technical significance, and any changes or modifications in the structures, the proportions, the sizes and the like should fall within the scope of the technical contents disclosed in the present disclosure as long as they do not affect the effects and the objectives achieved by the present disclosure. Meanwhile, the terms such as "first," "second" and "third" used in this specification are used for illustration purposes only, and are not intended to limit the scope of the present disclosure in any way. Any changes or modifications of the relative relationships of elements are therefore to be construed as within the scope of the present disclosure as long as there is no substantial change to the technical contents.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a system and a method for treating a cancer in a subject in need thereof.

Figure 1:
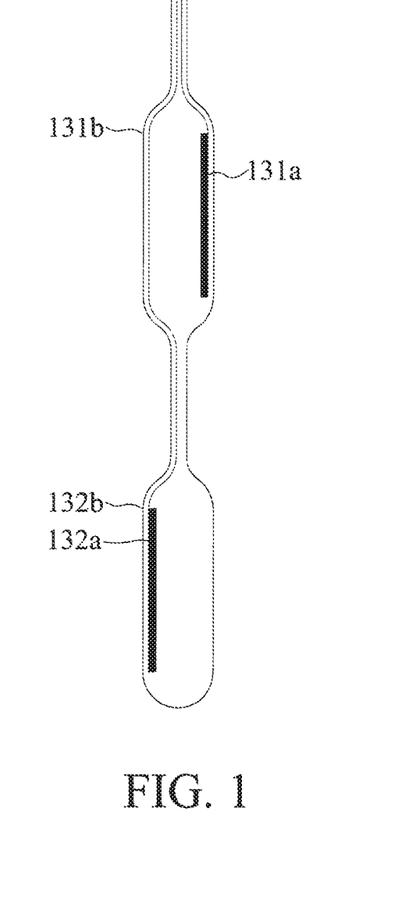
FIG. 1 is a diagram showing the heating apparatus in the system according to an embodiment of the present disclosure.

FIG. 1 is a diagram showing the heating apparatus in the system of the present disclosure. The heating apparatus comprises a first pouch 131b having a first inlet tube and a second pouch 132b having a second inlet tube connecting to the first pouch 131b, and a first RF electrode 131a in the first pouch 131b and a second RF electrode 132a in the second pouch 132b. The first RF electrode 131a and the second RF electrode 132a are configured to receive the RF signal.

The pouch can be made by any physiologically acceptable materials including, but not limited to, methylcellulose, hydroxypropyl methyl cellulose, sodium carboxymethyl cellulose, and/or polyvinylpyrrolidone (PVP), natural rubber, synthetic rubber, latex, polyurethane, membrane of intestines, silicone and the like. In an embodiment, the pouch is made by materials which are insoluble, soft, foldable and slightly flexible.

Figure 2:
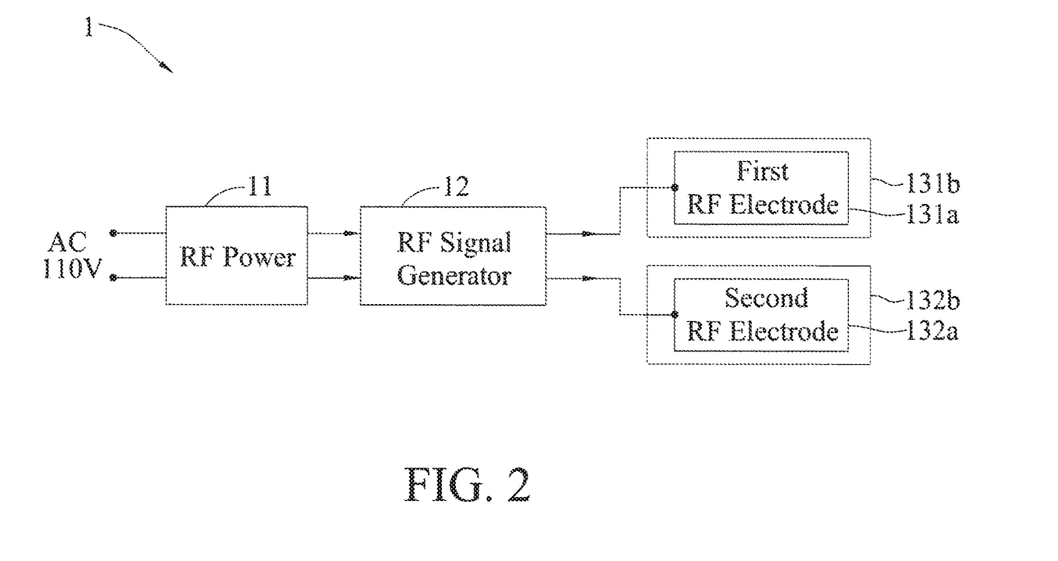
FIG. 2 is a diagram showing the configuration of the RF generator in the system according to an embodiment of the present disclosure.

FIG. 2 is a diagram showing the configuration of the RF generator in the system of the present disclosure. The system of the present disclosure comprises an RF generator 1 comprising an RF power 11 and an RF signal generator 12. The first RF electrode 131a in the first pouch 131b and the second RF electrode 132a in the second pouch 132b are connected with the RF signal generator 12.

The RF signal generator 12 electrically connects to the RF power 11. The RF signal generator 12 can be configured to be initiated by the RF power 11 and thus can generate an RF signal which can be transferred to a receiver.

After receiving the RF signal by the receiver, the receiver would generate a corresponding wave. In certain embodiments of the present disclosure, the receiver may be an RF electrode. As shown in FIGS. 1 and 2, the first RF electrode 131a can be disposed in the first pouch 131b. Similarly, the second RF electrode 132a can be disposed in the second pouch 132b.

According to some embodiments of the present disclosure, the RF electrode can be disposed in the pouch by any known means in the art. For example, the RF electrode can be separately disposed in the pouch. In other embodiments, the RF electrode can be a coated electrode that is coated on the inner surface of the pouch.

According to some embodiments of the present disclosure, after being initiated by the RF power 11, the RF signal generator 12 can generate a first RF signal and a second RF signal. The first and the second RF signals can be received by the first and the second RF electrodes 131a and 132a, respectively, and thus the RF generator 1 can generate a wave between the first RF electrode 131a and the second RF electrode 132a. In an embodiment, the wave generated by the RF generator 1 can have frequencies in a range of from 0.1 MHz to 100 MHz. In another embodiment, the wave generated by the RF generator 1 can have frequencies in a range of from 10 MHz to 100 MHz. In other embodiments, the lower limit of the frequencies may be 0.1 MHz, 0.5 MHz, 1 MHz, 2 MHz, 5 MHz, 10 MHz, 15 MHz, 20 MHz, 25 MHz, 30 MHz, 35 MHz, 40 MHz, 50 MHz or 60 MHz, and the upper limit of the frequencies may be 100 MHz, 90 MHz, 80 MHz, 70 MHz, 60 MHz, 50 MHz, 40 MHz or 30 MHz.

According to other embodiments, the first RF electrode 131a and the second RF electrode 132a can be connected as shown in FIG. 1. In the embodiment, the RF signal generator can generate an RF signal, which can be received by the first and second RF electrodes 131a and 132a, and thus the RF generator can generate a wave therebetween.

In some embodiments, the first pouch and the second pouch can be separated from each other. In other embodiments, the first pouch and the second pouch can be connected with each other.

Figure 3:
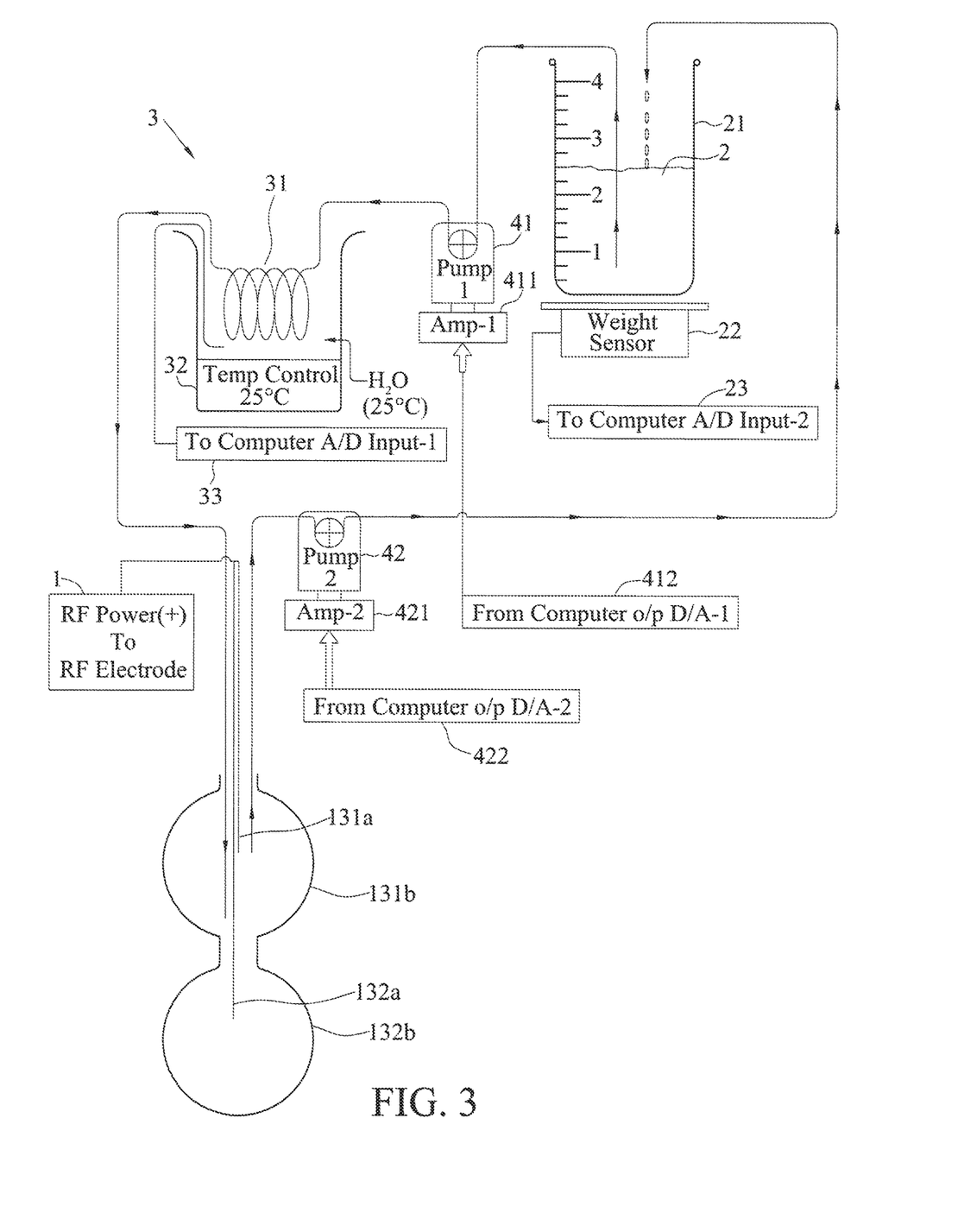
FIG. 3 is a diagram showing the configuration of the system according to an embodiment of the present disclosure.

FIG. 3 is a diagram showing the configuration of the system according to another embodiment of the present disclosure.

As shown in FIG. 3, in addition to the RF generator 1, the system can comprise a liquid reservoir 21. The liquid reservoir 21 can be operatively connected to the first inlet tube of the first pouch 131b and configured to supply liquid 2 to fill the first pouch 131b and the second pouch 132b.

According to the embodiments of the present disclosure, the liquid 2 is in a sufficient amount such that the system provided by the present disclosure can be full of the liquid when operating.

According to some embodiments of the present disclosure, the liquid 2 can be an aqueous solution. In some other embodiments, the aqueous solution can be a physiologically acceptable buffer solution.

The physiologically acceptable buffer solution can be any suitable buffer. The physiologically acceptable buffer solution used in the system of the present disclosure is not particularly limited and can be appropriately selected according to actual purposes. The physiologically acceptable buffer solution includes, but is not limited to, phosphate buffer, acetate buffer, citrate buffer, succinate buffer, histidine buffer and the like.

The liquid can be an aqueous solution of physiologically acceptable salts as well. The physiologically acceptable salts can be any physiologically acceptable soluble salts.

The physiologically acceptable salts are not particularly limited and can be appropriately selected according to actual purposes. The physiologically acceptable salts include, but are not limited to, physiologically acceptable inorganic salts selected from the group consisting of $NaCl$, $CaSO_4$, $CaCl_2$, $MgSO_4$, $MgCl_2$, $KCl$, and the like, as the form of water-free (anhydrous) or hydrated salts.

According to some embodiments of the present disclosure, the liquid 2 can be saline.

According to other embodiments of the present disclosure, the liquid 2 can be a physiologically acceptable liquid other than aqueous solutions.

As shown in FIG. 3, the liquid 2 is stored in a reservoir 21. The reservoir 21 can be equipped with a weight sensor 22 configured to monitor a volume of the liquid 2. Further, the weight sensor 22 can be controlled by a computer program. The weight sensor 22 can transfer sensing data to a computer through a computer A/D input 23.

Referring again to FIG. 3, the system of the present disclosure may comprise a temperature controller 3. The temperature controller 3 is configured to control the temperature of the liquid 2 before the liquid 2 is pumped into the first pouch 131b.

The temperature of the liquid 2 can be controlled by any temperature controller in any manner. The temperature controller is not particularly limited and can be appropriately selected according to actual purposes. An exemplary temperature controller is illustrated in FIG. 3.

The temperature controller 3 can comprise a heater module 32 that can include a tank filled with water at a desired temperature. The temperature of water in the tank can be controlled in the heater module 32, and its desired temperature can be about 25° C. or other temperatures, if needed. The heater module 32 can be further connected to a computer through a computer A/D input 33.

The temperature controller 3 also includes a heat exchanger 31. The heat exchanger 31 can be any type of heat exchangers in the art, for example, shell and tube heat exchanger, plate heat exchanger, plate and shell heat exchanger, adiabatic wheel heat exchanger, plate fin heat exchanger, pillow plate heat exchanger, fluid heat exchanger, waste heat recovery units, dynamic scraped surface heat exchanger, phase-change heat exchanger, direct contact heat exchanger, microchannel heat exchanger, and the like. The heat exchanger 31 can make the temperature of the liquid 2 the same as that of the water in the heater module 32.

In addition, the temperature controller 3 can further comprise a temperature monitor configured to monitor the temperature of the liquid 2.

In order to avoid overheating the liquid in the pouches, in addition to the temperature controller, the system of the present disclosure may be further equipped with at least two pumps.

As shown in FIG. 3, the system comprises at least two pumps, e.g., the first pump 41 and the second pump 42. The first pump 41 can be configured to draw the liquid 2 out from the liquid reservoir 21 and into the temperature controller 3. The first pump 41 can be electrified by the power supply 411 which can further be connected to a computer through a computer D/A input 412 to control the pumping speed of the first pump 41 as needed.

The second pump 42 can be configured to draw out the liquid 2 in the pouch and to move the liquid back into the liquid reservoir 21. The second pump 42 can also be electrified by the power supply 421 which can further be connected to a computer through a computer D/A input 422 to control the pumping speed of the second pump 42 as needed. In some embodiments, the numbers of the pumps can be more than two, if needed.

For example, the numbers of the pumps can be three, i.e., a first pump, a second pump, and a third pump. The first pump can be configured to draw the liquid out from the liquid reservoir into the temperature controller, and the second pump can be configured to draw out the liquid in the first pouch, while the third pump can be configured to draw the liquid in the second pouch back into the liquid reservoir. Alternatively, those pumps can be optionally used in series.

Referring to FIGS. 2 and 3, when the system provided by the present disclosure is in operation, the pouches 131b and 132b can be filled with the liquid 2. After the signals from the RF signal generator 12 have been received, radio frequency waves can be generated between the first RF electrode 131a and the second RF electrode 132a.

According to some embodiments of the present disclosure, the radio frequency waves warm the liquid 2 in the pouches 131b and 132b up to 27-50° C. In some embodiments, the temperature of the liquid in the pouches can be elevated up to 40-50° C.

The system of the present disclosure is useful for treating a cancer in a subject by heating a mass of the subject, wherein the mass can be a tumor and/or malignant cells.

The tumor and/or malignant cells can be selected from the group consisting of glioma, brain tumor, medulloblastoma, head and/or neck cancer, cervical cancer, nasopharynx cancer, thyroid cancer, bronchial cancer, breast cancer, mesothelioma, esophageal cancer, stomach cancer, pancreatic cancer, lung cancer, prostate cancer, cancer in bile cyst and/or bile duct, liver cancer, renal cell and/or renal pelvic cancer, ovarian cancer, rectal cancer, intestinal cancer, urinary tract cancer, endometrial cancer, vaginal cancer, testicular cancer, colon cancer, soft tissue cancer, Ewing's sarcoma, primary carcinoma, osteosarcoma, and a combination thereof.

According to some embodiments of the present disclosure, the system for treating a cancer in a subject in need thereof is useful for treating a cancer such as pancreatic cancer, lung cancer, prostate cancer or brain tumor.

In addition, the present disclosure provides a method for treating a cancer in a subject in need thereof by applying the system of the present disclosure to the subject. The method can comprise the following:
providing the system of the present disclosure;
positioning the first pouch into a first hollow capsule of the subject;
positioning the second pouch into a second hollow capsule of the subject;
filling the first pouch and the second pouch with the liquid;
initiating the RF signal generator to generate an RF signal, wherein the first RF electrode and the second RF electrode receive the RF signal; and
forming a wave to heat a mass of the subject within a hot zone between the first hollow capsule and the second hollow capsule.

According to the method of the present disclosure, the formed wave can have a frequency in a range of from 0.1 MHz to 100 MHz. In an embodiment, the wave can have a frequency in a range of from 10 MHz to 100 MHz. In other embodiments, the lower limit of the frequencies may be 0.1 MHz, 0.5 MHz, 1 MHz, 2 MHz, 5 MHz, 10 MHz, 15 MHz, 20 MHz, 25 MHz, 30 MHz, 35 MHz, 40 MHz, 50 MHz or 60 MHz, and the upper limit of the frequencies may be 100 MHz, 90 MHz, 80 MHz, 70 MHz, 60 MHz, 50 MHz, 40 MHz or 30 MHz.

According to some embodiments of the present disclosure, the formed wave can make the mass of the subject to be heated up to a temperature in a range of from 35° C. to 50° C. In an embodiment, the mass of the subject is heated up to a temperature in a range of from at least 38° C. to no more than 45° C. In another embodiment, the mass of the subject is heated up to about 42° C. In other embodiments, the mass of the subject is heated up to a temperature at a lower limit of 35° C., 37° C., 38° C., 39° C., 40° C., 41° C., 42° C., 43° C., 44° C., or 45° C. In another embodiments, the mass of the subject is heated up to a temperature at an upper limit of 50° C., 48° C., 47° C., 46° C., 45° C., 44° C., 43° C., 42° C., 41° C., or 40° C.

According to the method of the present disclosure, it can be used for treating a cancer or a mass in the subject in need thereof, wherein the mass can be a tumor and/or malignant cells.

According to the embodiments of the present disclosure, the tumor and/or malignant cells can be selected from the group consisting of glioma, brain tumor, medulloblastoma, head and/or neck cancer, cervical cancer, nasopharynx cancer, thyroid cancer, bronchial cancer, breast cancer, mesothelioma, esophageal cancer, stomach cancer, pancreatic cancer, lung cancer, prostate cancer, cancer in bile cyst and/or bile duct, liver cancer, renal cell and/or renal pelvic cancer, ovarian cancer, rectal cancer, intestinal cancer, urinary tract cancer, endometrial cancer, vaginal cancer, testicular cancer, colon cancer, soft tissue cancer, Ewing's sarcoma, primary carcinoma, osteosarcoma, and a combination thereof.

In certain embodiments of the present disclosure, the method is useful for treating a cancer such as pancreatic cancer, lung cancer or prostate cancer.

The system and the method provided by the present disclosure can be used as a supplement therapy in conjunction with any other well-known cancer therapy, such as radiation therapy, chemotherapy, surgery, anticancer drugs and the like.

It is believed that the additive, complementary effect of hyperthermia is due to the higher heat sensitivity of cells in the hypoxic and low-pH range, as well as the sensitivity of cells in the S phase; both of which are relatively radio-resistant. Moderate hyperthermia can also increase blood flow and thus increase tissue oxygenation, which results in increased radio-sensitivity. Hyperthermia increases cytotoxic radiation effects, particularly by interfering with the cellular repair system as a result of the denaturing of DNA. Hyperthermia can also enhance the effects of certain anticancer drugs.

Many examples have been used to illustrate the present disclosure. The examples below should not be taken as a limit to the scope of the disclosure.

EXAMPLE

Example 1

Figure 4:
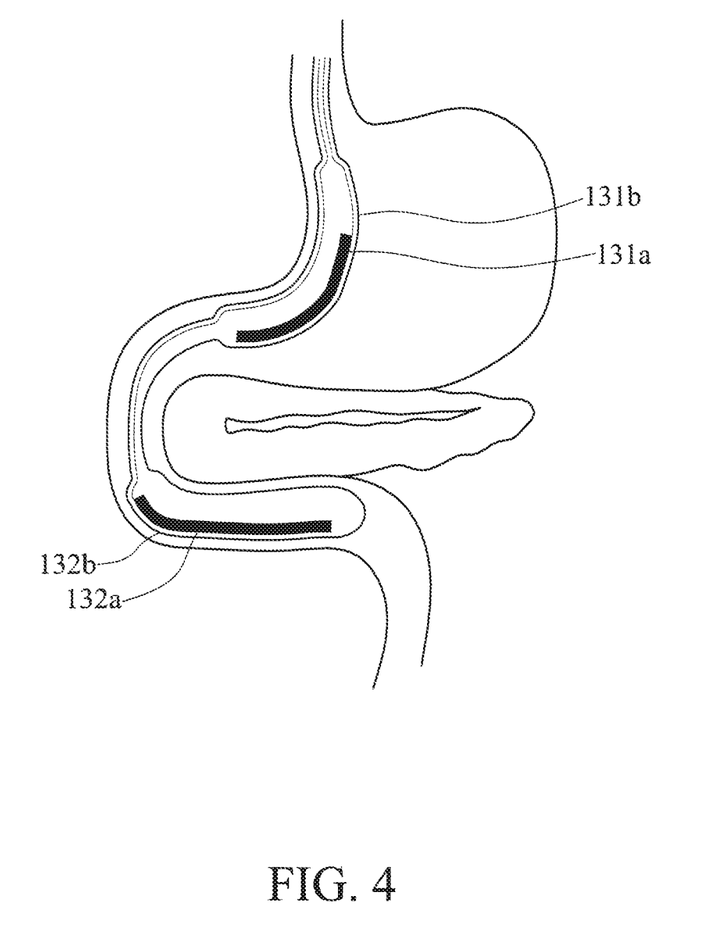
FIG. 4 is an illustration showing the system according to an embodiment of the present disclosure applied within a subject in need thereof for treating pancreatic cancer.

In a case of treating pancreatic cancer within a subject in need thereof, one of the examples of the system and the method using the same provided by the present disclosure is shown in FIG. 4.

FIG. 4 is an illustration showing the system according to an embodiment of the present disclosure applied within a subject in need thereof for treating pancreatic cancer.

The first pouch 131b comprising a first RF electrode 131a is positioned into a first hollow capsule of the subject. In this example, the first hollow capsule is the stomach of the subject.

The second pouch 132b comprising a second RF electrode 132a is positioned into a second hollow capsule of the subject. In this example, the second hollow capsule is the duodenum of the subject.

Then, by turning on the system of the present disclosure, the first pouch 131b and the second pouch 132b are filled with liquid, such as saline. The liquid is controlled at about 25° C. by the temperature controller. Next, the RF signal generator is initiated by the RF power so as to generate RF signals.

The first RF electrode and the second RF electrode receive the RF signals, and thus form waves with desired frequencies to create a hot zone between the stomach and the duodenum.

Due to the relative positions of the stomach, pancreas, and duodenum, the pancreas which located in the hot zone between the stomach and the duodenum is heated to about 35° C. to 50° C., or about 38° C. to 45° C. Such temperature is useful for treating pancreatic cancer. By heating the pancreas for a sufficient time period, the pancreatic cancer can be relieved or cured.

Example 2

Figure 5:
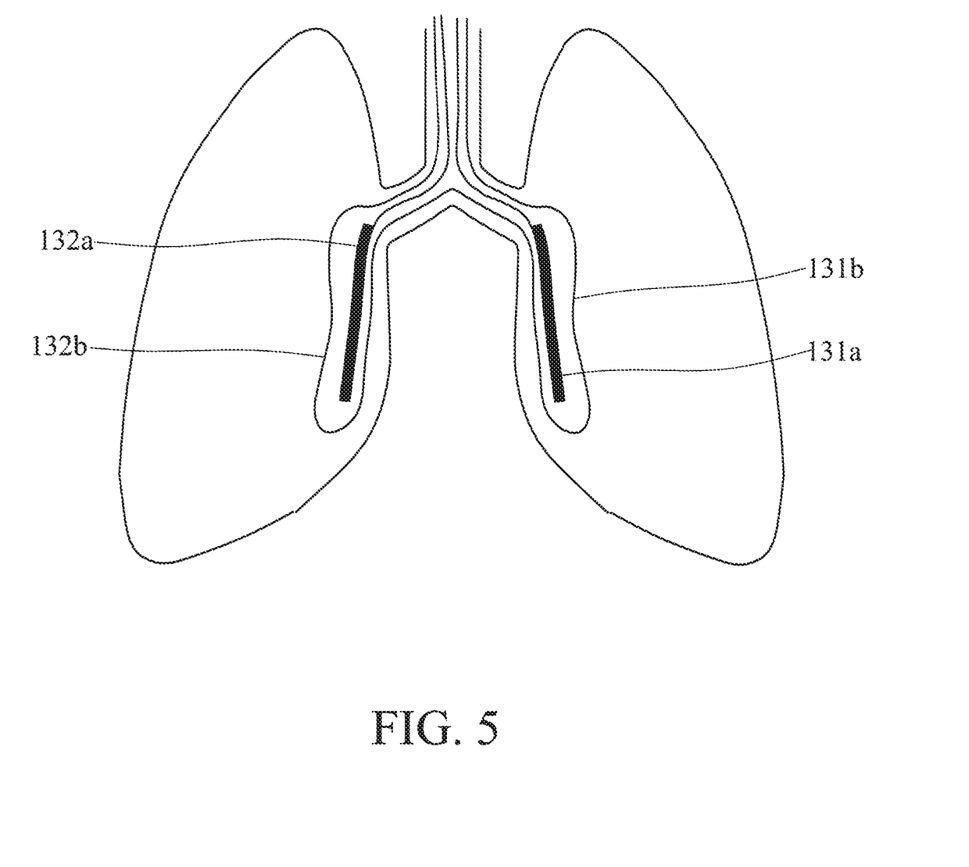
FIG. 5 is an illustration showing the system according to an embodiment of the present disclosure applied within a subject in need thereof for treating lung cancer.

In a case of treating lung cancer within a subject in need thereof, one of the examples of the system and the method using the same provided by the present disclosure is shown in FIG. 5.

FIG. 5 is an illustration showing the system according to an embodiment of the present disclosure applied within a subject in need thereof for treating lung cancer.

The first pouch 131b comprising a first RF electrode 131a is positioned into a first hollow capsule of the subject. The second pouch 132b comprising a second RF electrode 132a is positioned into a second hollow capsule of the subject. The first pouch 131b and the second pouch 132b have a first inlet tube and a second inlet tube, respectively, which are for connecting the second pouch 132b to the first pouch 131b.

Depending on the location of the malignant tumor in the lung, the first pouch 131b and the second pouch 132b can be positioned into the same or different lobe(s) of lung, such that the malignant tumor would lie between the first pouch 131b and the second pouch 132b. In this example, the first hollow capsule is the left lung of the subject, and the second hollow capsule is the right lung of the subject.

Then, by turning on the system of the present disclosure, the first pouch 131b and the second pouch 132b are filled with liquid, such as saline. The liquid is controlled at about 25° C. by the temperature controller. Next, the RF signal generator is initiated by the RF power so as to generate RF signals.

The first RF electrode and the second RF electrode receive the RF signals, and thus form waves with desired frequencies to create a hot zone between the right lung and the left lung.

The lung tumor is located in the hot zone and thus be heated to about 35° C. to 50° C., or about 38° C. to 45° C. Such temperature is useful for treating lung cancer. Therefore, by heating the tumor for a sufficient time period, the lung cancer can be relieved or cured.

Example 3

Figure 6:
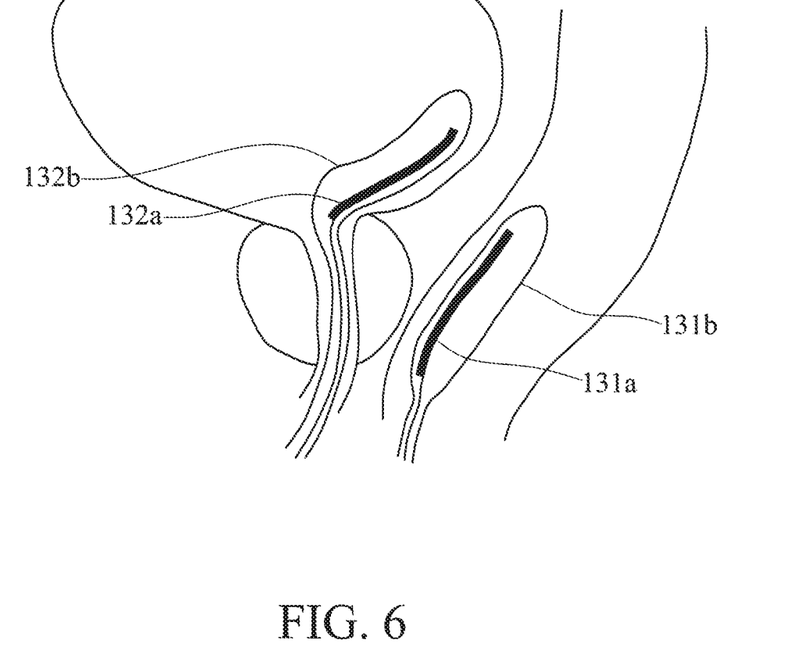
FIG. 6 is an illustration showing the system according to an embodiment of the present disclosure applied within a subject in need thereof for treating prostate cancer.

In a case of treating prostate cancer within a subject in need thereof, one of the examples of the system and the method using the same provided by the present disclosure is shown in FIG. 6.

FIG. 6 is an illustration showing the system according to an embodiment of the present disclosure within a subject in need thereof for treating prostate cancer.

The first pouch 131b comprising a first RF electrode 131a is positioned into a first hollow capsule of the subject. The second pouch 132b comprising a second RF electrode 132a is positioned into a second hollow capsule of the subject. The connection between the first pouch 131b and the second pouch 132b is not shown in the figure.

In this example, the first hollow capsule is the rectum of the subject, and the second hollow capsule is the bladder of the subject.

Then, by turning on the system of the present disclosure, the first pouch 131b and the second pouch 132b are filled with liquid, such as saline. The liquid is controlled at about 25° C. by the temperature controller. Next, the RF signal generator is initiated by the RF power so as to generate RF signals.

The first RF electrode and the second RF electrode receive the RF signals, and thus form waves with desired frequencies to create a hot zone between the rectum and the bladder.

Due to the relative positions of the rectum, prostate, and bladder, the prostate which located in the hot zone between the rectum and the bladder is heated to about 35° C. to 50° C., or about 38° C. to 45° C. Such temperature is useful for treating prostate cancer. By heating the pancreas for a sufficient time period, the prostate cancer can be relieved or cured.

It is evident that the system and the method using the same provided by the present disclosure have extremely excellent utility for treating a tumor and/or malignant cells within a subject in need thereof.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

The references listed below cited in the application are each incorporated by reference as if they were incorporated individually.

1. van der Zee J. Heating the patient: a promising approach? *Annals of Oncology* 2002; 13(8): 1173-1184.
2. Hildebrandt B, Wust P, Ahlers O, et al. The cellular and molecular basis of hyperthermia. *Critical Reviews in Oncology/Hematology* 2002; 43(1): 33-56.
3. Wust P, Hildebrandt B, Sreenivasa G, et al. Hyperthermia in combined treatment of cancer. *The Lancet Oncology* 2002; 3(8): 487-497.
4. Alexander H R. Isolation perfusion. In: DeVita V T Jr., Hellman S, Rosenberg S A, editors. *Cancer: Principles and Practice of Oncology*. Vol. 1 and 2. 6$^{th}$ ed. Philadelphia: Lippincott Williams and Wilkins, 2001.
5. Falk M H, Issels R D. Hyperthermia in oncology. *International Journal of Hyperthermia* 2001; 17(1): 1-18.
6. Dewhirst M W, Gibbs F A Jr., Roemer R B, Samulski T V. Hyperthermia. In: Gunderson L L, Tepper J E, editors.

*Clinical Radiation Oncology.* 1$^{st}$ ed. New York, NY: Churchill Livingstone, 2000.
7. Kapp D S, Hahn G M, Carlson R W. Principles of Hyperthermia. In: Bast R C Jr., Kufe D W, Pollock R E, et al., editors. *Cancer Medicine* e.5.5$^{th}$ ed. Hamilton, Ontario: B.C. Decker Inc., 2000.

What is claimed is:

1. A system for treating pancreatic cancer in a subject in need thereof, comprising:
   a radio frequency (RF) generator, comprising:
      an RF power; and
      an RF signal generator electrically connected to the RF power, wherein the RF signal generator is configured to be initiated by the RF power and generate an RF signal; and
   a heating apparatus having a first end and a second end, and consisting essentially of:
      a first non-porous pouch disposed at the first end of the heating apparatus with a first inlet tube and configured to be positioned into a first hollow capsule of the subject;
      a second non-porous pouch disposed at the second end of the heating apparatus with a second inlet tube and configured to be positioned into a second hollow capsule of the subject, wherein the first hollow capsule is a stomach of the subject, and the second hollow capsule is a duodenum of the subject;
      a pair of electrodes, wherein one of the pair of electrodes is a first coated RF electrode coated on an inner surface of the first non-porous pouch and the other of the pair of electrodes is a second coated RF electrode coated on an inner surface of the second non-porous pouch, and wherein the first coated RF electrode and the second coated RF electrode are configured to receive the RF signal, and the number of the electrodes between the first end and the second end in the heating apparatus is two; and
      a liquid reservoir operatively connected to the first inlet tube of the first non-porous pouch and configured to supply liquid to fill the first non-porous pouch and the second non-porous pouch,
   wherein the RF generator is configured to generate a wave with a frequency between the first coated RF electrode and the second coated RF electrode to heat a mass of the subject within a hot zone between the first hollow capsule and the second hollow capsule.

2. The system of claim 1, wherein the first coated RF electrode and the second coated RF electrode are connected with the RF signal generator via a wire.

3. The system of claim 1, wherein the first coated RF electrode and the second coated RF electrode are wire electrodes.

4. The system of claim 1, further comprising a temperature controller configured to control a temperature of the liquid.

5. The system of claim 4, further comprising:
   a first pump configured to draw the liquid out from the liquid reservoir into the temperature controller; and
   a second pump configured to draw out the liquid in the first non-porous pouch and the second non-porous pouch back into the liquid reservoir.

6. The system of claim 4, wherein the temperature controller comprises:
   a heater module including a tank filled with water at a desired temperature controlled in the heater module;
   a heat exchanger configured to make the temperature of the liquid the same as that of the water in the heater module; and
   a temperature monitor configured to monitor the temperature of the liquid.

7. The system of claim 1, wherein the liquid reservoir comprises a weight sensor configured to monitor a volume of the liquid.

8. The system of claim 1, wherein the frequency of the wave is in a range of from 0.1 MHz to 100 MHz.

9. The system of claim 1, wherein the frequency of the wave is in a range of from 10 MHz to 100 MHz.

10. The system of claim 1, wherein the liquid is an aqueous solution.

11. The system of claim 10, wherein the aqueous solution is a physiologically acceptable buffer solution or a salt thereof, or saline.

12. A method for treating pancreatic cancer in a subject in need thereof, comprising:
   providing the system according to claim 1;
   positioning the first non-porous pouch into the first hollow capsule of the subject;
   positioning the second non-porous pouch into the second hollow capsule of the subject, wherein the first hollow capsule is a stomach of the subject, and the second hollow capsule is a duodenum of the subject;
   filling the first non-porous pouch and the second non-porous pouch with the liquid;
   initiating the RF signal generator to generate the RF signal, wherein the first coated RF electrode and the second coated RF electrode receive the RF signal; and
   forming the wave to heat the mass of the subject within the hot zone between the first hollow capsule and the second hollow capsule.

13. The method of claim 12, wherein the wave has a frequency in a range of from 0.1 MHz to 100 MHz.

14. The method of claim 12, wherein the wave has a frequency in a range of from 10 MHz to 100 MHz.

15. The method of claim 12, wherein the mass is a tumor or a malignant cell.

16. The method of claim 12, wherein the mass of the subject is heated up to at least 38° C. and no more than 45° C.

17. The method of claim 16, wherein the mass of the subject is heated up to 42° C.

\* \* \* \* \*